Dec. 6, 1960 H. L. GEBHARD ET AL Plant Pat. 1,992
PEAR TREE
Filed Dec. 7, 1959
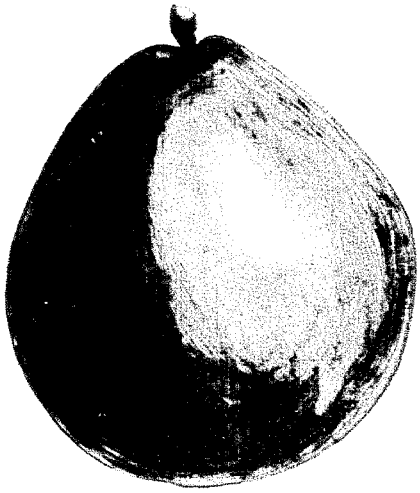
INVENTORS
Harold L. Gebhard and
Edward W. Gebhard, deceased
By Lucille M. Gebhard and
Marjorie A. Grigsby, executrix
BY Ramsey and Kolisch
Attys.

United States Patent Office

Plant Pat. 1,992
Patented Dec. 6, 1960

1,992

PEAR TREE

Harold L. Gebhard, deceased, and Edward W. Gebhard, deceased, both late of Medford, Oreg.; by Lucille M. Gebhard, Rt. 2, Box 640, Central Point, Oreg., and Marjorie A. Grigsby, 230 Franklin Bldg., Medford, Oreg., executrices Filed Dec. 7, 1959, Ser. No. 858,003

1 Claim. (Cl. 47—62)

This discovery relates to a new and distinct variety of pear tree, and more particularly to a sport of the pear tree commonly known as the Anjou or Beurre d'Anjou, a variety of nonpatented pear.

A particularly distinguishing feature of the new variety of pear tree is the distinctive coloring of its fruit. The pear at picking time and when ready for eating has a deep reddish coloring, as compared to the yellowish-green coloring which characterizes the ordinary Anjou pear tree. The pear tree is further distinguishable from its parent in that the bark and veins of the leaves of the pear tree have a reddish overcast, particularly noticeable in young growth. In other particulars, the pear is similar to the ordinary Anjou, i.e., the pear has a shape, flesh coloring, texture, and flavor similar to that of the parent.

The distinctive reddish coloring of the pear increases its marketability, as the coloring is appealing and attractive to buyers.

Accompanying this specification is a drawing illustrating in color and substantially in elevation the new variety of pear.

The pear tree was discovered and asexually reproduced in a cultivated area in the county of Jackson, Oregon, in the vicinity of Medford, Oregon, and originated as a limb sport. Asexual reproduction was by grafting, such grafting illustrating that the distinctive reddish coloring of the pear was established and transmitted through succeeding propagations.

Below there appears a detailed description of the new variety of pear tree, such description being based upon observations of pear specimens and with reference to botanical authorities. The predominant color identified for the pear was identified with reference to colors designated in Robert Ridgway's "Color Standards and Nomenclature," published in 1912.

Tree: Substantially upright; hardy; vigorous; spreading.

*Branches.*—Slightly zigzagged; few small lenticels; relatively smooth.

*Leaves.*—Fairly abundant foliage; leaf buds are small, short, obtuse; leaves at maturity elongated, oval, thin, leathery, approximately 3½ inches long and 1½ inches wide; apex taper pointed; margins nearly entire or crenate; petiole approximately 2 inches long. Veins and petiole have a reddish cast, particularly noticeable in young growth and viewing the underside of a leaf.

*Flowers.*—Floral buds large, long, conical; flowers in dense clusters, 8–12 buds in a cluster; blooming date in Medford in 1958 was March 16, in 1959, April 5; harvest date in 1958 was September 11, in 1959, September 15 (when harvested green and in condition for canning). Pears formed within about a week after date of bloom. (NOTE.—the summer of 1959 was relatively dry in the Medford area and the pears were harvested later than usual.)

Fruit:—Fairly good keeping quality. Eating ripe approximately 10 days after picking. Fruit placed in cold storage in good condition in December.

*Size.*—Medium to fairly large; uniform shape; sides slightly unequal; generally globular in shape, sometimes slightly pyriform.

*Skin.*—Clear when grown in dry climates; tender; smooth; somewhat dull.

*Stem.*—Quite short, about 1½ inch in length; thick and woody; fairly straight.

*Basin.*—Shallow; narrow; obtuse; smooth; symmetrical and regular.

*Core.*—Large; closed; core-lines clasping.

*Calyx tube.*—Short; wide; conical.

*Seeds.*—Large; wide; long; plump; acuminate; tufted at the tips.

*Flesh.*—Yellowish-white in color; fairly fine; buttery; slightly granular; firm but tender; juicy.

*Flavor.*—Aromatic; spicy; rich; sweet.

*Color.*—General effect of overall dark red color. Color identification with reference to the color authority noted above showed the dominant color to be Vandyke Red, as designated on Plate XIII.

What is claimed is:

A new and distinct variety of pear tree, substantially as shown and described herein, distinguished principally from its parent, the Anjou, by the overall dark red coloring of the fruit skin.

No reference cited.